United States Patent
Duncan et al.

(10) Patent No.: US 12,357,670 B2
(45) Date of Patent: *Jul. 15, 2025

(54) TOPICAL CREAM-BASED COSMETIC AND WOUND HEALING FORMULATIONS AND METHODS OF USE

(71) Applicant: Eir Pharmaceuticals, LLC, Olathe, KS (US)

(72) Inventors: William P Duncan, Olathe, KS (US); Lauren S Gollahon, Lubbock, TX (US); William C Putnam, Frisco, TX (US)

(73) Assignee: EIR Pharmaceuticals, LLC, Olathe, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/115,929

(22) Filed: Mar. 1, 2023

(65) Prior Publication Data
US 2023/0201296 A1    Jun. 29, 2023

Related U.S. Application Data

(63) Continuation of application No. 16/686,535, filed on Nov. 18, 2019, now Pat. No. 11,607,438, which is a continuation-in-part of application No. 16/590,807, filed on Oct. 2, 2019, now Pat. No. 11,622,987.

(60) Provisional application No. 62/788,261, filed on Jan. 4, 2019, provisional application No. 62/740,047, filed on Oct. 2, 2018.

(51) Int. Cl.
| | | |
|---|---|---|
| A61K 36/00 | (2006.01) | |
| A61K 8/19 | (2006.01) | |
| A61K 8/34 | (2006.01) | |
| A61K 8/37 | (2006.01) | |
| A61K 8/64 | (2006.01) | |
| A61K 8/97 | (2017.01) | |
| A61K 8/98 | (2006.01) | |
| A61K 9/06 | (2006.01) | |
| A61K 31/198 | (2006.01) | |
| A61K 36/886 | (2006.01) | |
| A61K 47/02 | (2006.01) | |
| A61K 47/10 | (2017.01) | |
| A61K 47/44 | (2017.01) | |
| A61P 17/02 | (2006.01) | |
| A61Q 19/00 | (2006.01) | |

(52) U.S. Cl.
CPC .............. *A61K 36/886* (2013.01); *A61K 8/19* (2013.01); *A61K 8/342* (2013.01); *A61K 8/345* (2013.01); *A61K 8/347* (2013.01); *A61K 8/375* (2013.01); *A61K 8/64* (2013.01); *A61K 8/97* (2013.01); *A61K 8/987* (2013.01); *A61K 9/06* (2013.01); *A61K 31/198* (2013.01); *A61K 47/02* (2013.01); *A61K 47/10* (2013.01); *A61K 47/44* (2013.01); *A61P 17/02* (2018.01); *A61Q 19/00* (2013.01); *A61K 2236/30* (2013.01); *A61K 2800/592* (2013.01)

(58) Field of Classification Search
None
See application file for complete search history.

*Primary Examiner* — Russell G Fiebig
(74) *Attorney, Agent, or Firm* — Christopher M DeBacker

(57) ABSTRACT

A cream formulation or topical use made of a mixture of naturally occurring biologically active phytochemical compounds that possess a variety of beneficial animal and human health effects. An extract from an aqueous extraction process or other active ingredients could be used in the cream formulation. The present invention generally provides for the preparation of cream formulations containing active ingredients that contain individually, or in combination, an analgesic, natural product extracts, or a protein or proteins from the tripartite motif family of proteins (TRIM). The analgesic will provide mitigation of pain during the healing process.

7 Claims, 12 Drawing Sheets

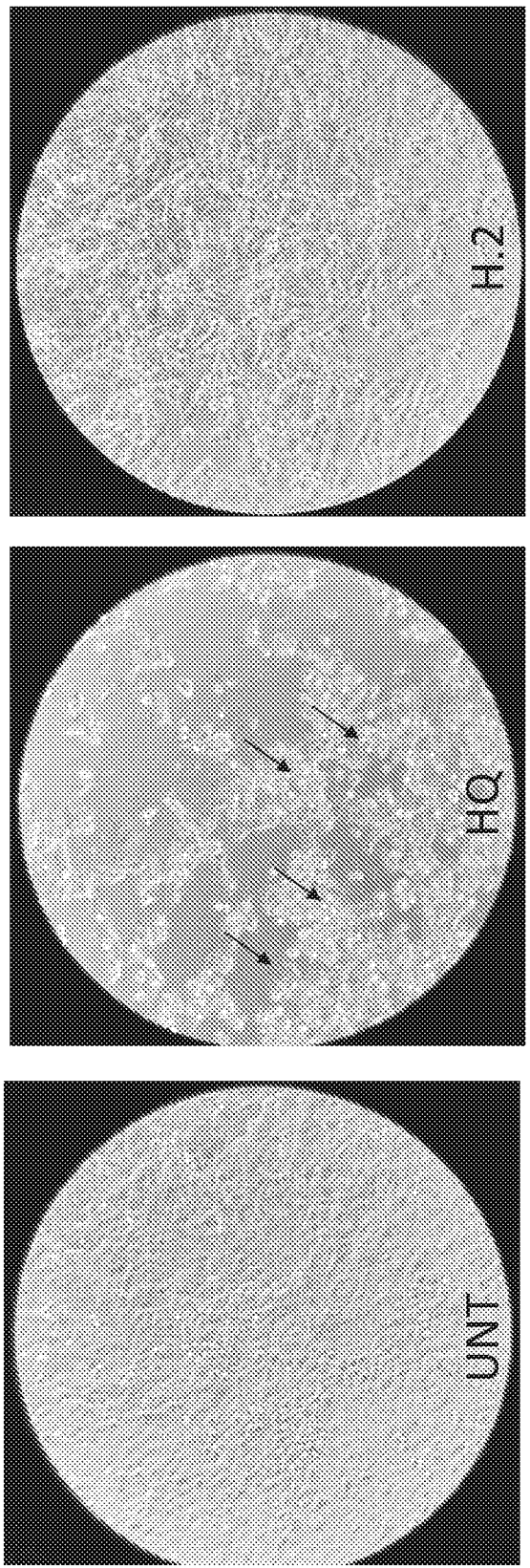
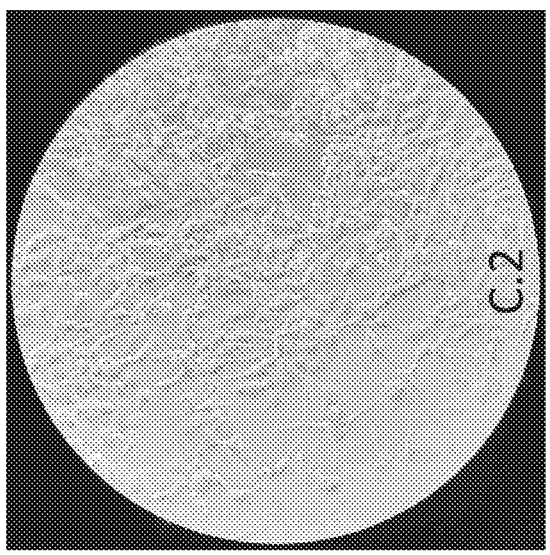
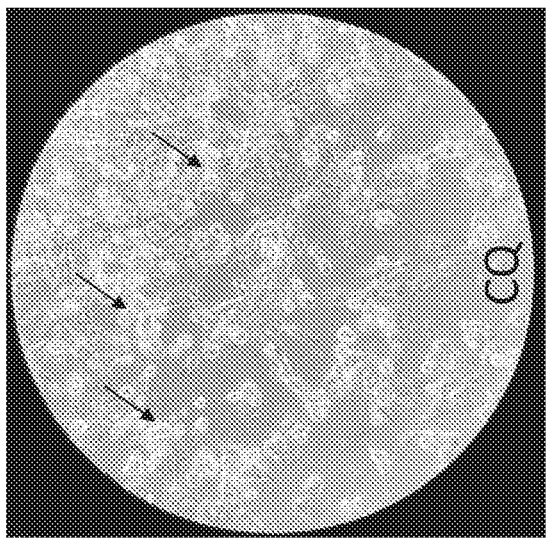
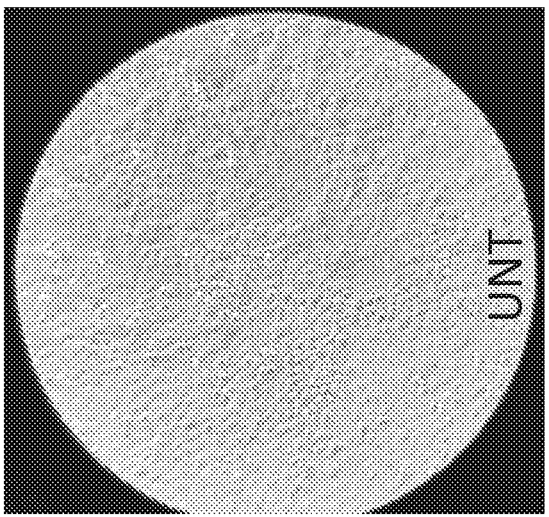
FIG. 5

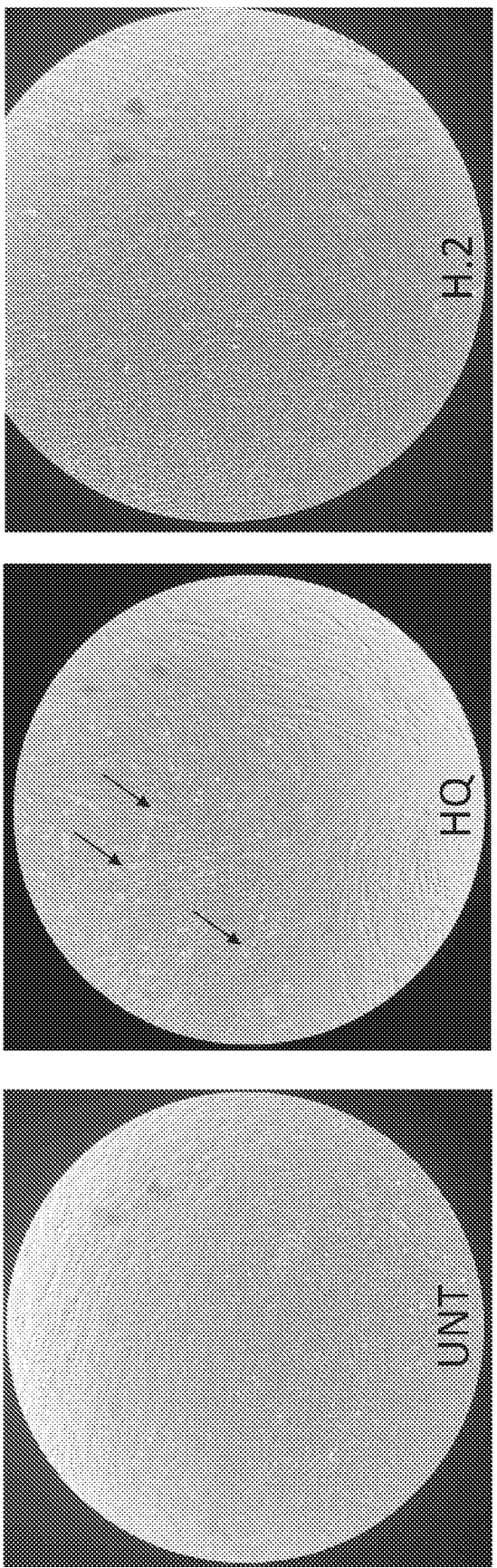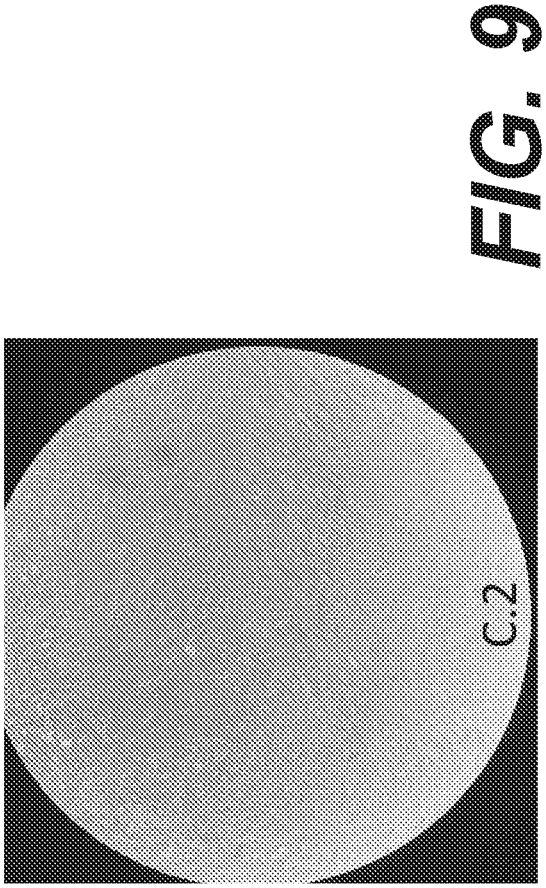
FIG. 9

TOPICAL CREAM-BASED COSMETIC AND WOUND HEALING FORMULATIONS AND METHODS OF USE

CROSS-REFERENCE TO RELATED APPLICATION

This application is a continuation of U.S. patent application Ser. No. 16/686,535, Filed Nov. 18, 2019, which is a continuation-in-part of and claims priority in U.S. patent application Ser. No. 16/590,807 filed Oct. 2, 2019 which, claims priority in U.S. Provisional Patent Application No. 62/740,047 filed Oct. 2, 2018, and this application also claims priority in U.S. Provisional Patent Application No. 62/768,261 filed Nov. 16, 2018 all of which are incorporated herein by reference.

BACKGROUND OF THE INVENTION

1. Field of the Invention

The present invention relates generally to a cream-based topical substance, and more specifically to cream-based compositions applied to the skin for cosmetic, sun-protectant, wound treatment, and anti-scarring purposes and the process and methods for the preparation thereof. In one exemplary embodiment, the cosmetic, wound treatment and anti-scarring formulation comprises a naturally occurring protein within the topically applied cream.

2. Description of the Related Art

Existing methods for extracting key compounds or components for generating a chemical composition comprised of an extract thereof do exist. However, these processes have failed to adequately and reliably produce a chemical composition having the results of the present invention.

Cosmetic, anti-sun and wound treatment creams are well known. These types of topically applied compositions are frequently made with a petroleum base designed to deliver active constituents to the dermis. Cosmetic creams typically include a hydrocarbon base in combination with the active constituents. Occlusive natural oils and synthetic long-chain hydrocarbons have been used in construction of makeup and foundation bases imparting sheen, function as binders for components in the formulation and form the basis of the oil phase of conventional emulsion systems.

Physicians often prescribe wound treatment creams to patients to expedite healing of wounds and to reduce scarring. Depending on the cause of wounds, e.g. surgery, injury, disease related, etc, many are often difficult to heal due to infection or other sequela complications. In addition, temporary cosmetic side effects, such as swelling, bruising, or visible scars commonly result from plastic surgery or other injuries to the skin. It may take days, weeks, or even months before wounds heal and such side effects disappear. Historically, wound treatment creams and cosmetic creams have been used to promote healing and to disguise skin wounds.

Heretofore there has not been available a system or method for cream-based topical substance and resulting benefits with the advantages and features of the present invention.

BRIEF SUMMARY OF THE INVENTION

The present invention generally provides for the preparation of an aqueous extract resulting from an aqueous extraction of individual or mixtures of *Cinnamomum cassia, Arctium lappa, Vitex agnus castus, Lonicera japonica, Acanthopanax gracilistylis, Raphanus sativus, Astragalus membranaceus* and *Hordeum vulgare* and the chemical composition comprising said extracts or fractions thereof, and the use of said compositions or fractions thereof for treating or preventing cancers and inflammation related diseases, hair loss, stimulating hair growth, increasing energy production, and boosting immunity.

One use of the extract could be used in the preparation of a cream formulation for topical use. Other active ingredients could be used in the cream formulation in place of the extract. The present invention generally provides for the preparation of cream formulations containing active ingredients that contain individually, or in combination, an analgesic, natural product extracts, or a protein or proteins from the tripartite motif family of proteins (TRIM). The analgesic will provide mitigation of pain during the healing process. The natural product extracts are generated from plants that are known to decrease inflammation, stimulate immune response and promote repair in damaged cells. The TRIM proteins are naturally occurring proteins in mammalian and animal cells known to be important in cell membrane maintenance and repair and infection resistance. One aspect of the invention includes cream-based formulations containing inorganic salts that are particularly well suited for use on open wounds that can be applied topically to the skin to simultaneously repair and disguise wounds on human and animal skin. Another aspect of the invention includes cream-based formulations containing inorganic salts that are particularly well suited for use as a preventative for damage done to the skin due to exposure to the sun. Another aspect of the invention includes a method of preparing stable cream formulations that prevents degradation of the natural product extracts or TRIM proteins.

The resulting extracts include a mixture of naturally occurring biologically active phytochemical compounds that possess a variety of beneficial animal and human health effects.

BRIEF DESCRIPTION OF THE DRAWINGS

The drawings constitute a part of this specification and include exemplary embodiments of the present invention illustrating various objects and features thereof.

FIG. 5 shows a series of cells visualized with a microscope on day 5 of the bar graph of FIG. 4.

FIG. 9 shows a series of cells visualized with a microscope on day 5 of the bar graph of FIG. 8.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed manifestation.

Certain terminology will be used in the following description for convenience in reference only and will not be limiting. For example, up, down, front, back, right and left refer to the invention as orientated in the view being referred to which the referral is directed. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

Figure 1:
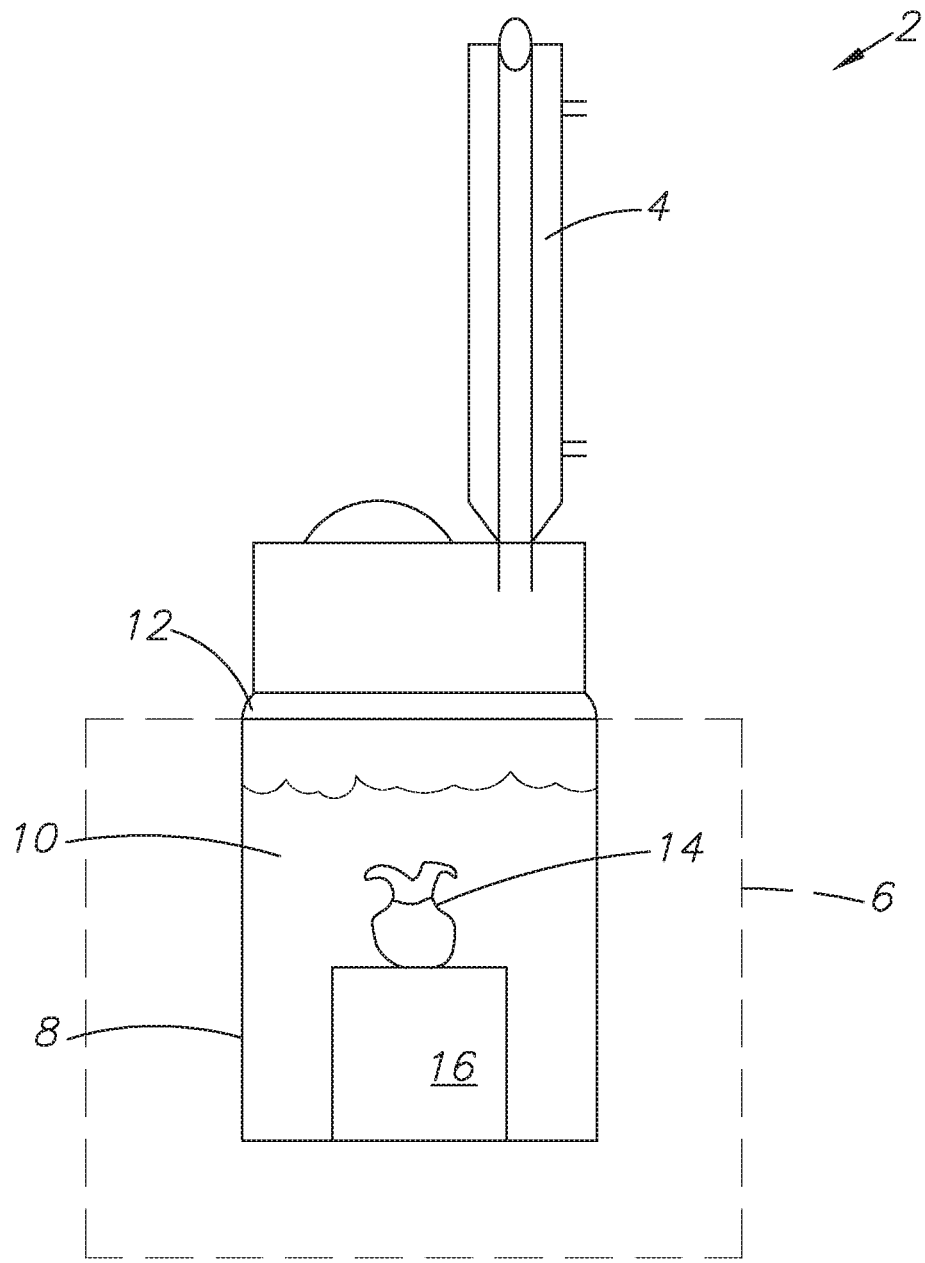
FIG. 1 is a diagram of a preferred embodiment static (batch) aqueous extraction system.

II. Preferred Embodiment Static (Batch) System and Aqueous Extraction Process FIG. 1 shows a static aqueous extraction system 2. A process utilizing this static system 2 results in a product capable of producing desired results as described in more detail and in specific examples below.

Individual or a desired mixture of *Cinnamomum cassia, Arctium lappa, Vitex agnus castus, Lonicera japonica, Acanthopanax gracilistylis, Raphanus sativus, Astragalus membranaceus* and *Hordeum vulgare* are combined in equal or various amounts by dry weight and placed in a spunbond nonwoven fabric container 14. The fabric container may be placed upon a pedestal 16 within the extraction apparatus 8 for optimal results. The spunbond nonwoven fabric container 14 is sealed and then fixed within the extraction apparatus 8 containing reverse-osmosis membrane filtered purified or distilled water 10 as shown in FIG. 1. The extraction apparatus may be made of a stainless steel or glass vessel. The extraction apparatus 8 is contained within a heating element 6. The extraction apparatus is closed and sealed with a seal 12 and then heated such that the water 10 is boiling for 3-6 hrs. Some of the vapor is discharged through the water-cooled condenser outlet 4 affixed to the top of the extraction apparatus 8 allowing some volatiles to escape while retaining a portion that are condensed and returned to the extraction apparatus. The seal retains the condenser unit 4 in connection with the extraction apparatus 8. The resulting extraction mixture is then filtered in succession using a membrane filter with a pore size not bigger than 10-6 m (1 micron) and purified water at 90-100° C., 70-85° C., 40-60° C., 15-30° C., and 5-15° C., providing the final product filtrate (extract) that contains ~370 mg of biologically active solid ingredients per liter of aqueous extract. Example compounds identified in the aqueous extract include acids such a chlorogenic and cinnamic acid, aldehydes, e.g. cinnamaldehyde and lignans, e.g. archin.

For example, by dry weight, for each liter of water, 220 mg of *Cinnamomum cassia,* 110 mg *Arctium lappa,* 220 mg *Vitex agnus castus,* 110 mg *Lonicera japonica,* 110 mg *Acanthopanax gracilistylis,* 110 mg *Raphanus sativus,* 110 mg *Astragalus membranaceus* and 220 mg *Hordeum vulgare* are combined and placed in a spunbond nonwoven fabric, and the spunbond nonwoven fabric sealed and then fixed within the extraction apparatus filled with reverse-osmosis membrane filter purified or distilled water. The extraction vessel is closed and then heated to boiling for 3 hrs. Some of the vapor is discharged through the water-cooled condenser outlet affixed to the top of the extraction vessel allowing a portion of volatiles to escape while retaining some that are condensed and returned to the extraction vessel. The resulting hot extraction mixture, of these ingredients is referred to as, EPE001, from this point onward, is then filtered in succession via simple vacuum assisted filtration using membrane filters with a pore size not bigger than 10-6 m (1 micron) at 90-100° C., 70-85° C., 40-60° C., 15-30° C., and 5-15° C. providing the final product extract that contains ~370 mg of biologically active solid ingredients per liter of aqueous extract.

III. Alternative Embodiment Dynamic (Semi-Continuous Flow) System and Aqueous Extraction Process 52

Figure 2:
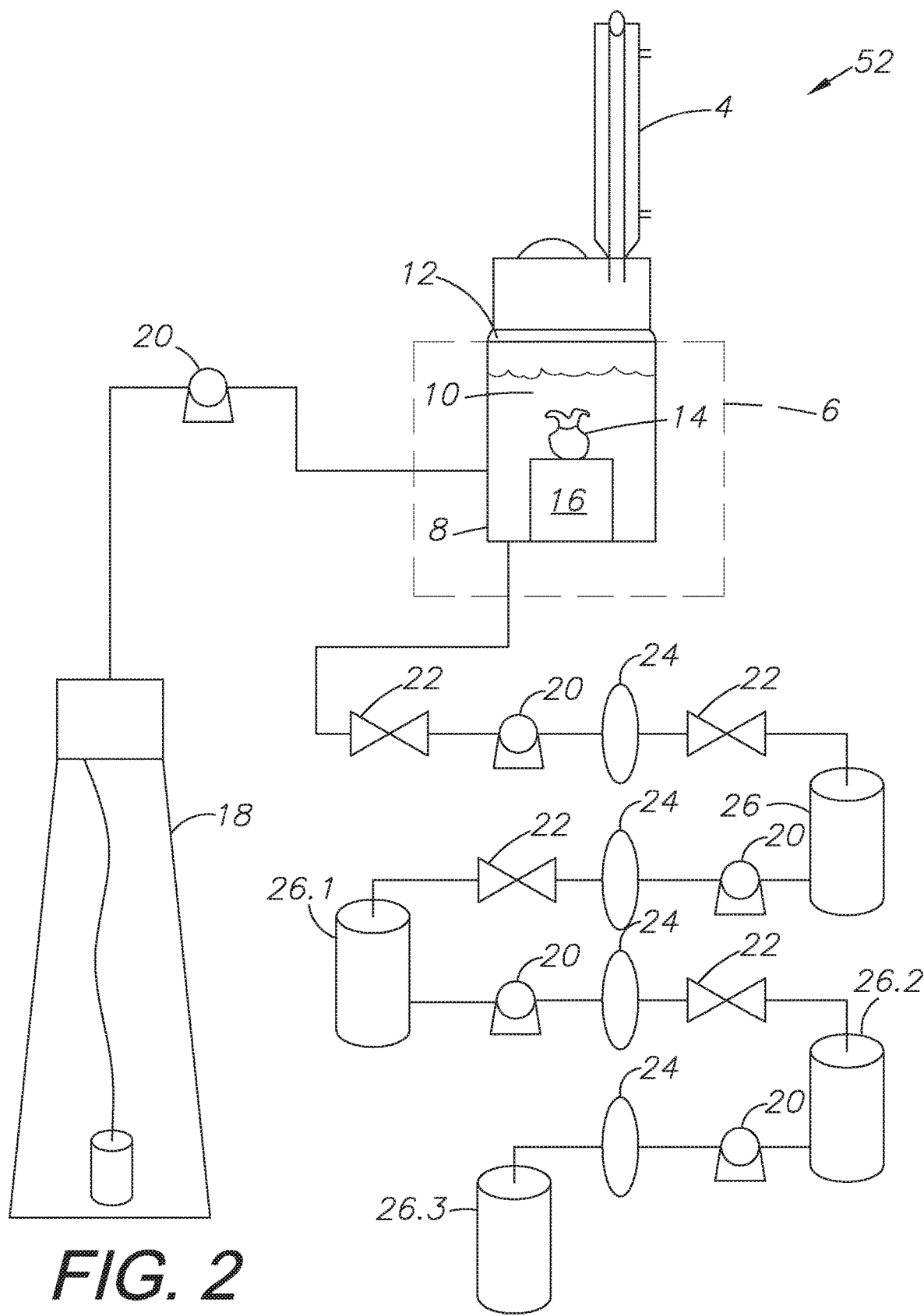
FIG. 2 is a diagram of an alternative embodiment dynamic (semi-continuous flow) aqueous extraction system.

FIG. 2 presents an alternative system for producing an extract from an aqueous extraction process utilizing a dynamic system 52. In the same manner as the static system 2, an individual herb or a desired mixture of *Cinnamomum cassia, Arctium lappa, Vitex agnus castus, Lonicera japonica, Acanthopanax gracilistylis, Raphanus sativus, Astragalus membranaceus* and *Hordeum vulgare*, are combined in equal or various amounts by dry weight and placed in a spunbond nonwoven fabric container 14, and the spunbond nonwoven fabric container 14 is sealed and then fixed within the extraction vessel 8. Reverse-osmosis membrane filter purified, or distilled water 10 is then pumped into the extraction vessel 8 via a pump 20. The extraction apparatus 8 is contained within a heating element 6. The extraction apparatus is closed and sealed with a seal 12 and heated to boiling for 4-6 hrs. Some of the vapor is discharged through the water-cooled condenser outlet 4 affixed to the top of the extraction vessel allowing some volatiles to escape while retaining some that are condensed and returned to the extraction vessel. The resulting extraction mixture, EPE001, is then filtered in succession by pressure driven filtration using filters with a pore size not bigger than 10-6 m (1 micron) utilizing a system of appropriately connected pumps and valves that allow for efficient transfer of the purified water extract at 70-95° C., followed by filtering the extract using purified water at 70-95° C., 40-60° C., 15-30°

C., and 5-15° C., providing the final product extract that contains ~350 mg of active solid ingredients per liter of aqueous extract. This extraction process allows for a dynamic semi-continuous flow production of biologically active extract by pausing the process, recharging the spunbond nonwoven fabric with selected amounts of dried herbs and initiating the process by pumping purified water 10 into the extraction vessel 8 and restarting the heating device.

This process is made dynamic through the use of a large vessel of purified water 18 which is pumped using a pump 20 into the extraction vessel 8. It is then pulled out of the extraction vessel 8 using a series of valves 22, filters 24, and pumps 20 as shown in FIG. 2 into one or more storage containers 26, 26.1, 26.2, 26.3. The system can be run dynamically until all storage containers are filled, and as soon as there is volume in one storage container as shown, the aqueous extract can pass into the next pump and filter set. Purified water can be pumped into the vessel 8 from the reservoir 18 through an inlet in the reservoir near the top of the vessel. After the boiling step is complete, the aqueous extract can be pumped out through an outlet near the bottom of the vessel and through a single or series of decreasing pore-size filters with the final filter being a 0.2 μm filter. The filtrate would then be dispensed into a collection vessel as a finished product for a number of various uses.

The use of the extract resulting from the aqueous extraction processes as described herein are varied. A first use of the extract would be as a potential cancer therapeutic. This would provide an application to a broad range of solid cancers (neoplasias) due to effects of the extract chemical composition on mitochondrial function in cancer cells (e.g. apoptosis, autophagy, and mitochondrial membrane potential changes) as well as changes in transcriptional activation (promote or inhibit) of key genes associated with cancer progression or suppression. The benefits include a reduction or elimination of side effects common in existing cancer therapeutics. The preparation of the extract as presented herein provides for the delivery of biologically active compounds topically or as an aqueous oral dose. It has a bioactivation and bioavailability increase upon digestion associated with changes in pH. It causes a decrease in the proliferation of cancer cells and an inhibition of genes related to cancer cell growth.

A second use of the extract as presented herein would be an anti-inflammatory therapeutic. It provides a reduction in reactive oxygen species formation in normal cells. It reduces production of inflammatory cytokines. It also provides increased mobility with concurrent decrease in joint pain.

A third use is as an energy supplement. The extract provides an increase in beta-oxidation utilizing fatty acids as a substrate for generation of ATP. It provides increased energy production (e.g. mitochondrial efficiency). It also provides a decrease in glucose dependency as a metabolic substrate, while also reducing inflammation as described above.

A fourth use is as a weight loss supplement. The extract has been shown to increase beta-oxidation utilizing fatty acids as a substrate for generation of ATP, and a decrease in glucose dependency as a metabolic substrate. The extract has also been shown to decrease glucose dependency as a metabolic substrate. These metabolic changes are expected to cause weight loss. The extract has also been shown to provide an inhibition of some known obesity related gene expression.

A fifth use is for its antiviral effectiveness due to increased potential cell membrane resistance and decreased replication capabilities against clinically relevant viral strains including HIV, Influenza Virus, West Nile Virus, Adenovirus, and Polymavirus.

A sixth use is for its antimicrobial effectiveness due to its effectiveness against pathogenic bacterial infections including, *Streptococcus* sp., *Staphylococcus* sp., and *Listeria* sp.

A seventh use is for dermatological stem cell activity, such as for use for hair growth or other uses against skin conditions such as atopic dermatitis, psoriasis, and eczema.

An eighth use is for boosting the immune system. Specifically, inducing pluripotent stem cells to replace depleted populations of T-cell lymphocytes. This population replenishment has direct positive benefits in the mechanism of action and is described in [0027] and [0028].

IV. Examples and Results Utilizing a Product by Process of Static (Batch) System and Aqueous Extraction Process 2 or Dynamic (Semi-Continuous Flow) System and Aqueous Extraction Process 52

FIGS. 3-9 show several examples and results thereof utilizing a product produced by the processes described above. Other examples are not explicitly shown, but the results are described below. Typical treatments for cancer involve chemicals that are not only toxic to infected cells but also other surrounding cells, tissues and systems. Because of this there is a growing need and interest for utilizing natural products for treatment of a variety of human diseases and conditions. Using the herein described process, a reproducible, aqueous extract of a combination of plants has been shown to be toxic to human cultured cancer cells but does not harm healthy cells.

Figure 3:
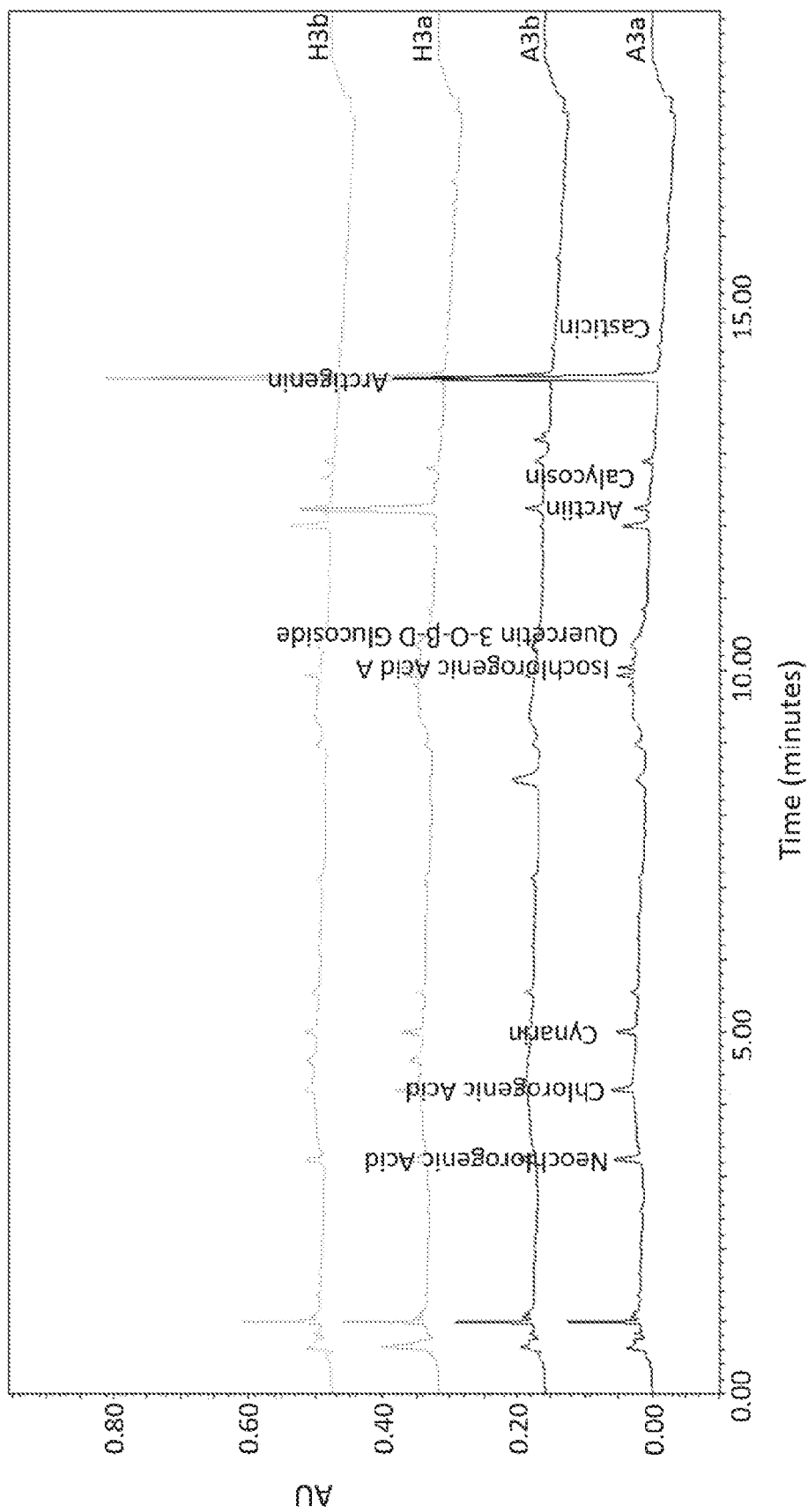
FIG. 3 is a LC chromatogram depicting the components of an exemplary product (EPE001) of an extraction process utilizing one of the embodiments of the extraction systems of FIGS. 1 and 2.

In these examples, each of the eight herbs (*Cinnamomum cassia, Arctium lappa, Vitex agnus castus, Lonicera japonica, Acanthopanax gracilistylis, Raphanus sativus, Astragalus membranaceus* and *Hordeum vulgare*) were milled to a powder then passed through a 0.21 mm mesh sieve to exclude any large particulates. The powders were combined and placed into a spunbond nonwoven fabric bag and sealed then placed into a vessel containing reverse-osmosis purified water utilizing the static system 2 shown in FIG. 1 and alternatively the dynamic continuous system 52 shown in FIG. 2. After the vessel was sealed, the water was brought to a boil for 3 hours. The aqueous extract (EPE001) was split into four aliquots. Two aliquots were cooled to 80° C. before passing through either a qualitative filter (11 μm) or a 0.2 μm filter. The other two aliquots were allowed to cool to room temperature before being passed through either a qualitative filter (11 μm) or a 0.2 μm filter. A portion of each aliquot was lyophilized to dryness before being diluted with purified water to a final concentration of 3.6 mg extract residue per milliliter. Each of these samples were then utilized in analytical experimentation and bioassays to determine chemical composition and biological activity FIG. 3 shows a graph wherein each of the four samples were analyzed using a Waters ACQUITY UPLC-PDA-MS system. Major components were identified by mass, then verified through comparison to a prepared standard of the isolated molecule to confirm the identity. Major components of the extract are: arctigenin, cholorgenic acid, neocholorgenic acid, isochlorogenic acid A, arctiin, quercetin 3-O-β-D glucoside, cyanarin and casticin. Other components of the extract have not yet been identified. Sample collected from the extraction process was lyophilized to dryness and resuspended to a final concentration of 3.6 mg/mL in 0.1% formic acid (pH 4.2). Chromatography was achieved using a 20 μL injection volume and a Waters ACQUITY UPLC HSS T3, 100 Å, 2.1×100 mm, column. A gradient elution was used with Mobile Phase A of 0.1% formic acid (pH 4.2) and Mobile Phase B of 80:20 acetonitrile:water. The linear chromatographic gradient started with 95% Mobile Phase A and concluded with 5% Mobile Phase A over 19.1 minutes with a flow rate of 0.4 mL/min. Chromatograms were collected monitoring the column effluent at 236 nm with a UV/Vis detector and with a Single-Quadrapole (QDa) mass spectrometer set to monitor a mass range of 50-1200 Da. Samples were: EPE001 filtered at −80° C. through an 11 μm qualitative filter (H3a), EPE001 filtered at −80° C. through a 0.2 μm filter (H3b), EPE001 cooled to room temperature before filtration through an 11 μm qualitative filter (A3a), and EPE001 cooled to room temperature before filtration through a 0.2 μm filter (A3b).

V. Additional Examples

Figure 4:
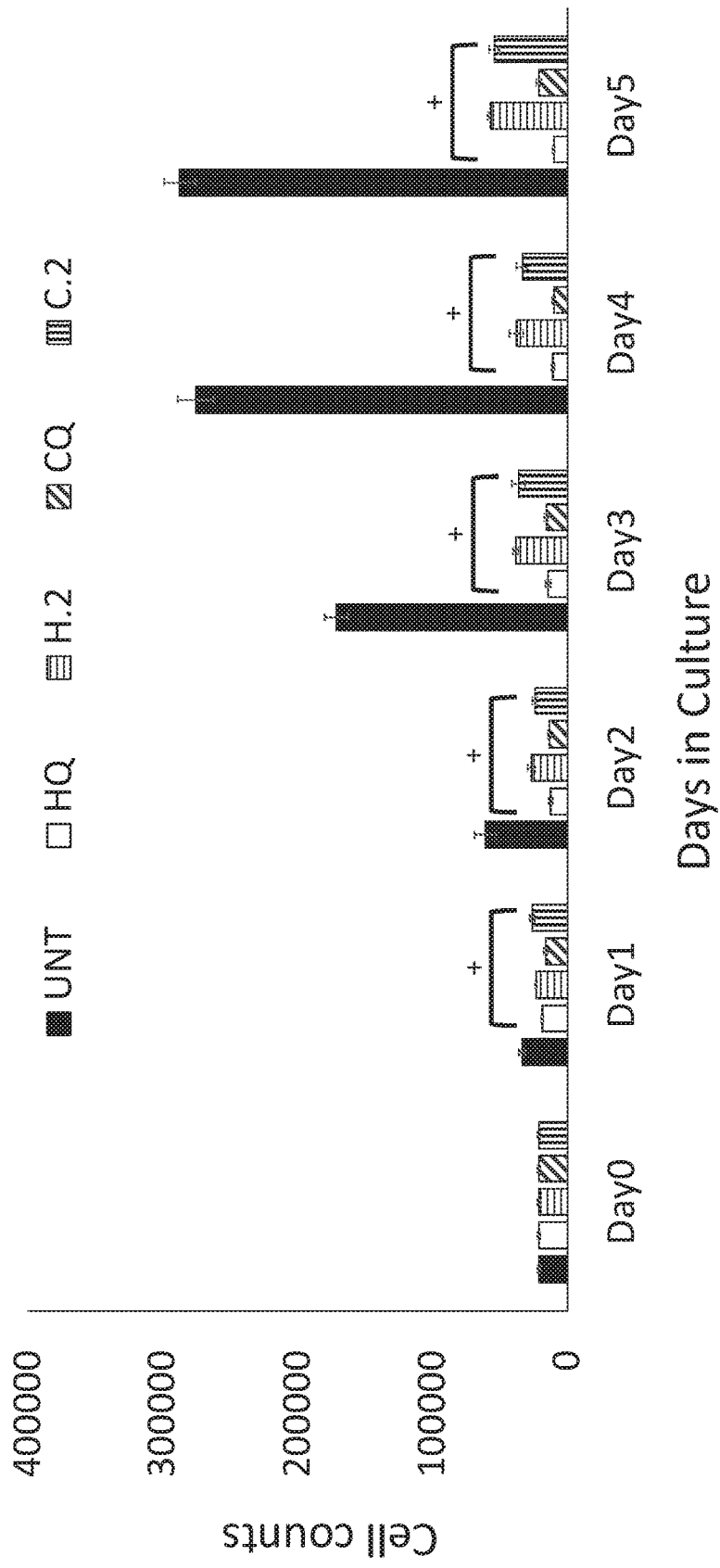
FIG. 4 is a bar graph depicting results of a treatment of human breast cancer cells utilizing a product produced by the process resulting from the embodiments of either FIG. 1 or FIG. 2.

FIGS. 4 and 5 are treatments of human breast cancer cells treated with an exemplary product of the extraction process (EPE001). 20,000 MCF7 (human breast adenocarcinoma) cells were seeded in 48 well plates in triplicate, allowed to adhere for 24 hours before treatment commenced (Day 0). Treatment groups were each performed in triplicate and include: untreated control group (UNT), treated with EPE001 filtered at −80° C. through an 11 μm qualitative filter (HQ), treated with EPE001 filtered at −80° C. through a 0.2 μm filter (H.2), treated with EPE001 cooled to room temperature before filtration through an 11 μm qualitative filter (CQ), and treated with EPE001 cooled to room temperature before filtration through a 0.2 μm filter (C.2). Cells were photographed and counted every 24 hours for 5 days. Images at Day 5 are represented in FIG. 5.

FIG. 4 shows the results in the form of a bar graph of applying each of the four filtered versions of EPE001 to MCF7 cells which are cultured human breast cancer cells. Control group samples that received no treatment (UNT) rose from 20,000 cells at day 0 to nearly 300,000 cells by the end of day 5. All applications of the example extract have a statistically significant (ANOVA p-value <0.05) impact on the growth of the cancer cells. By day 5, EPE001 filtered with the qualitative (11 μM) filter at 80° C. had the greatest cytotoxic effect, decreasing the original cell count by 28-fold in comparison to a 14× increase in cell count for the control group. Extract treated cancer cells not only showed strong cytotoxic effects, but also displayed an effect on the morphology of the cells as shown in FIG. 5. Treated cancer cells show changes in cell membrane permeability, diameter, volume and shape (rounder) as well as becoming less adherent to the microplate surface—suggesting multiple mechanisms of action resulting in cytotoxicity. Arrows indicate condensed cytoplasmic constituents, loss of membrane integrity and cell-cell as well as cell-substrate adhesion. When comparing the UNT cells to EPE001 treated samples, it is evident that there is significant cell loss. Furthermore, where the UNT cells look smooth and very confluent, cytoplasmic extension, stress and cell death features such as vacuolization and membrane blebbing.

Figure 6:
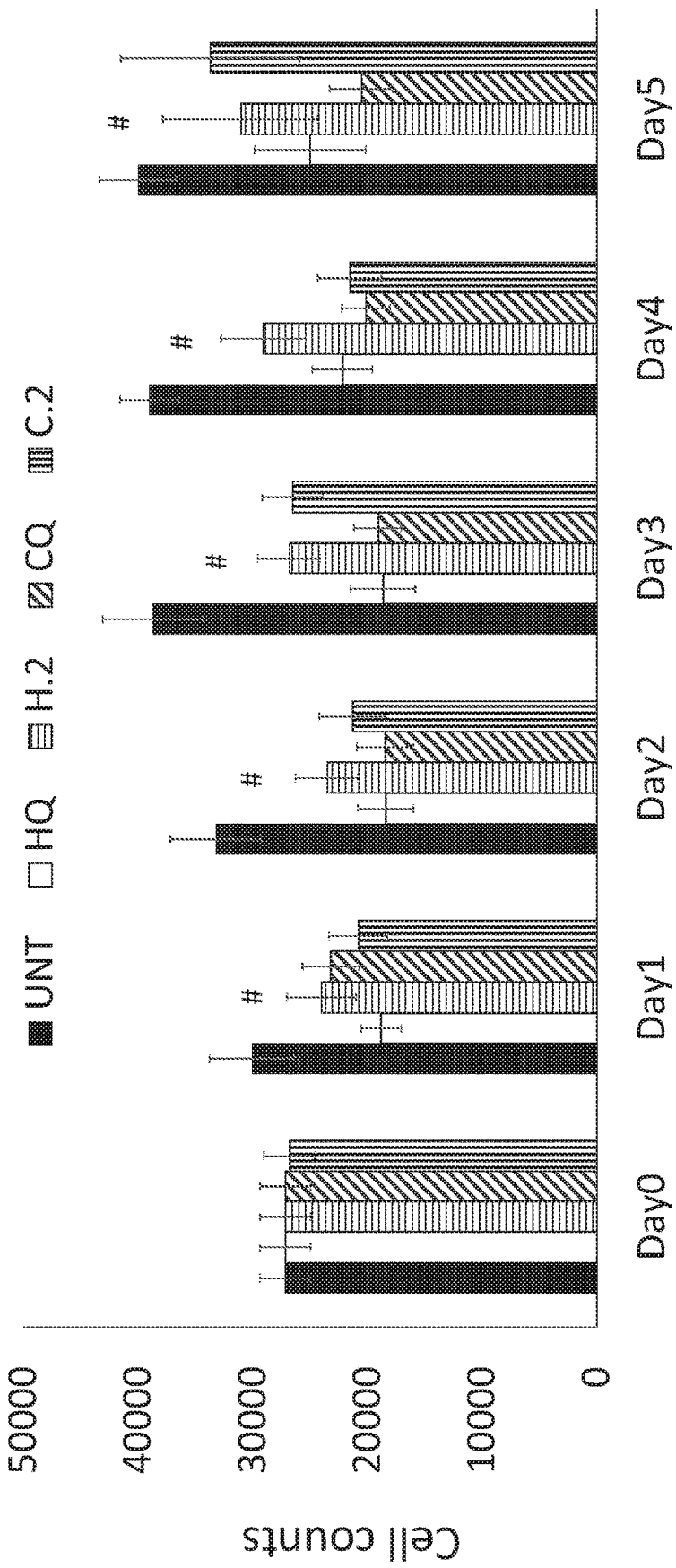
FIG. 6 is a bar graph depicting results of a treatment of human epithelial cells utilizing a product produced by the process resulting from the embodiments of either FIG. 1 or FIG. 2.
Figure 7:
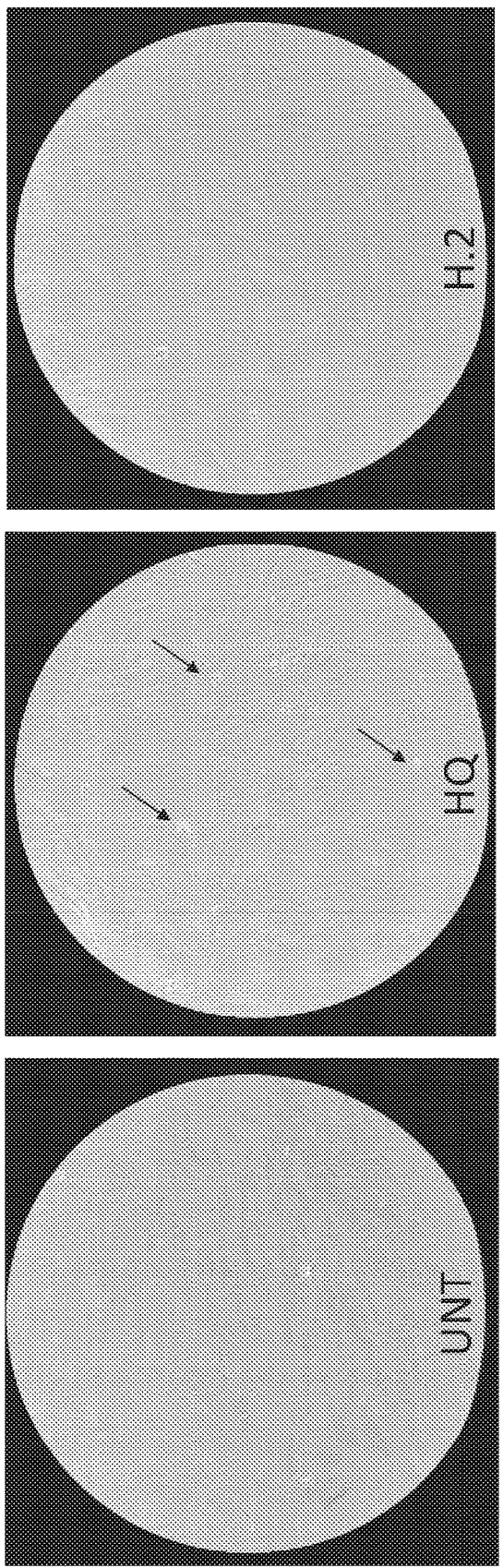
FIG. 7 shows a series of cells visualized with a microscope on day 5 of the bar graph of FIG. 6.

Similarly, FIG. 6 and FIG. 7 are treatments of healthy human epithelial cells with an exemplary product of the extraction process (EPE001). 20,000 MCF10A (normal, human mammary epithelial) cells were seeded in 48 well plates in triplicate, allowed to adhere for 24 hours before treatment commenced (Day 0). Treatment groups were each performed in triplicate and include: untreated control group (UNT), treated with EPE001 filtered at −80° C. through an 11 μm qualitative filter (HQ), treated with EPE001 filtered at −80° C. through a 0.2 μm filter (H.2), treated with EPE001 cooled to room temperature before filtration through an 11 μm qualitative filter (CQ), and treated with EPE001 cooled to room temperature before filtration through a 0.2 μm filter (C.2). Cells were photographed and counted every 24 hours for 5 days Images at Day 5 are represented in FIG. 7.

FIG. 6 shows the results in the form of a bar graph of applying each of the four filtered versions of EPE001 were applied to MCF10A cells which are cultured human normal epithelial breast cells. Control group samples that received no treatment rose from 20,000 cells at Day 0 to ~40,000 cells by the end of day 5. It should be noted that normal mammary epithelial cells grow more slowly and are constrained by area and cell-cell interactions whereas cancer cells grow much faster and are not constrained either by confluence or cell-cell boundaries. EPE001 filtered with the 0.2 μm filter at 80° C. did not have a statistically significant change in cell count by the end of day 5 (ANOVA p-value >0.05, meaning there is no statistical significance in the comparison).

Figure 8:
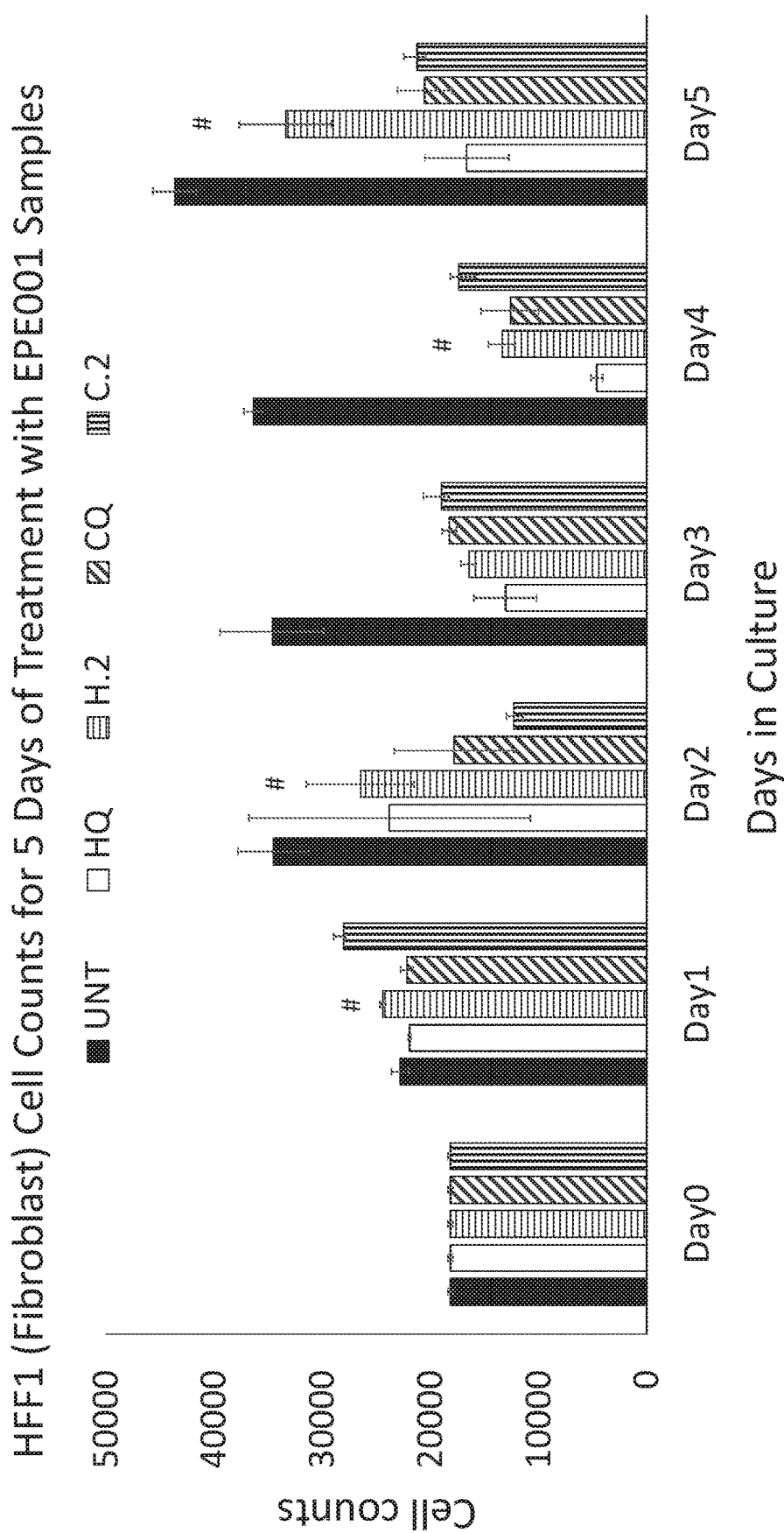
FIG. 8 is a bar graph depicting results of a treatment of fibroblast cells utilizing a product produced by the process resulting from the embodiments of either FIG. 1 or FIG. 2.

Cells treated with the 0.2 μm filtered EPE001 did not show morphological differences, as shown in FIG. 7, from untreated cells. Cells treated with the qualitative filter (11 μM) EPE001 did show slight morphological differences with some cytotoxicity. Additionally, cells treated with EPE001 became more adherent to the walls of the microplate, which may account for some of the cell count differences between treated cells and the untreated control samples. Given that epithelial cells serve as barriers for the body, this adherent property was considered beneficial FIG. 8 shows the results in the form of a bar graph of applying each of the four filtered versions of EPE001 were applied to HFF1 cells which are cultured human normal foreskin fibroblast cells. Control group samples that received no treatment proliferated from 20,000 cells at day 0 to ~45,000 cells by the end of day 5. It should be noted that normal fibroblast cells grow more slowly and are constrained by area and cell-cell interactions whereas cancer cells grow much faster and are not constrained either by confluence or cell-cell boundaries. EPE001 filtered with the 0.2 μm filter at 80° C. did not have a statistically significant change in cell count by the end of day 5 (ANOVA p-value >0.05, meaning there is no statistical significance in the comparison).

Cells treated with EPE001 filtered with the 0.2 μm filter at 80° C. did not show morphological differences in comparison to the untreated control group as shown in FIG. 9. However, the other filtration versions of EPE001 showed loss of cells, increased cell size and more strongly delineated boundaries. As with the epithelial cells, fibroblast cells treated with EPE001 became more adherent to the walls of the microplate, which may account for some of the cell count differences between treated cells and the untreated control samples. In this case, stronger adherence is positive attribute, especially since fibroblast cells comprise the structural framework of connective tissues and play key roles in wound healing.

VI. RNA-Seq Analysis of Changes in Gene Regulation Due to Extract

RNA-Seq analysis or Whole Transcriptome Shotgun Sequencing (WTSS) uses a Next-Generation Sequencing (NGS) method to catalog and count the number of RNA transcripts produced in a selected cell culture. This technique can be used as a comparative tool to determine which genes are activated or suppressed and to what degree in different environments—in this example, with and without the presence of the Extract Product. Data collected from RNA-Seq analysis is analyzed utilizing a web-based software application, Ingenuity Pathway Analysis (IPA), produced by QIAGEN Bioinformatics.

TABLE A

Top Upstream Regulators

| Name | p-value | Predicted Activation |
|---|---|---|
| Upstream Regulators | | |
| HGF | 1.99E–13 | Inhibited |
| NUPR1 | 4.63E–13 | Activated |
| Vegf | 2.71E–12 | Inhibited |
| TP53 | 1.64E–09 | Activated |
| E2F4 | 1.93E–09 | |
| Causal Network | | |
| HSPG2 | 1.59E–13 | Inhibited |
| NUPR1 | 3.11E–13 | Activated |
| axitinib | 4.29E–13 | Activated |
| Vegf | 7.94E–13 | Inhibited |
| HGF | 2.73E–12 | Inhibited |

Table A is a summary of gene expression changes in the presence of an exemplary product of the extraction process (EPE001) using RNA-Seq analysis. MCF7 (human breast adenocarcinoma) cells were seeded at 1×10^6 cells in T25 flasks and incubated at 37° C., 5% CO2 for 24 hours. Cells were allowed to adhere for 24 hours before treatment commenced. Cells were treated with medium only (reference sample) or treated with EPE001 and allowed to incubate for 24 hours. Cells were harvested and RNA was isolated using a Qiagen RNeasy Mini Kit as per manufacturer instruction. RNA transcriptome was sequenced using an Illumina MiSeq system. FASTQ files were generated by the Illumina CASAVA v1.8.2 and the quality of reads was evaluated by NGSQC Toolkit v2.3. High-quality reads were mapped, annotated to exons, and normalized to FPKM values for all 25,278 human RNA references in NCBI RefSeq database. Differential gene expression analysis was determined using DNAstar software. Biological pathway analyses were carried out using Ingenuity Pathway Analysis (Qiagen).

For this example, untreated MCF7 breast cancer cells were used as a control. The differences between this control and the MCF7 breast cancer cells treated with EPE001 (filtered at 80° C. with a 0.2 μm filter) using RNA-Seq analysis. Table A above represents the IPA software output of genes upregulated (increase in the physical number of RNA transcripts produced for a particular gene) or downregulated (decrease in the physical number of RNA transcripts produced for a particular gene) in the presence of the Extract Product.

The gene, HGF (hepatocyte growth factor), is involved in cell growth and has higher expression in cancer cells. This gene is downregulated in the presence of EPE001.

The gene, VEGF (vascular endothelial growth factor), has been implicated in promoting blood supply to cancer cells and the metastatic cascade. This gene is downregulated in the presence of EPE001.

The gene, HSPG2 (heparan sulfate proteoglycan 2), is involved in angiogenesis, β-amyloid binding, abnormal morphology and cell proliferation. This gene is also downregulated in the presence of EPE001.

The gene, TP53 (tumor protein 53), is a well-studied tumor suppressor gene that is involved in regulation of cell death and prevention of proliferation. This gene is upregulated in the presence of EPE001.

The gene, NUPR1 (nuclear protein 1), regulates cell death and signals TP53, which is a tumor suppressor gene. This gene is upregulated in the presence of EPE001.

In summary, important upstream regulator genes associated with cancer proliferation are downregulated in the presence of the Extract Product. Important upstream master tumor suppressor genes are upregulated in the presence of EPE001. The RNA-Seq analysis coincides with the physical results seen in FIGS. 4 and 5.

TABLE B

Summary Analyses of IPA of Top Diseases and Associated Networks

Top Diseases and Bio Functions
Diseases and Disorders

| Name | p-value range | # Molecules |
|---|---|---|
| Cancer | 9.59E–05–6.48E–146 | 2248 |
| Organismal Injury and Abnormalities | 9.81E–05–6.48E–146 | 2259 |

Top Networks

| ID | Associated Network Functions | Score |
|---|---|---|
| 1 | DNA Replication, Recombination and Repair, Embryonic Development, Nervous System Development and Function | 39 |
| 2 | Organismal Injury and Abnormalities, Reproductive System Disease, Cancer | 37 |
| 3 | Carbohydrate Metabolism, Small Molecule Biochemistry, Psychological Disorders | 37 |
| 4 | Carbohydrate Metabolism, Lipid Metabolism, Small Molecule Biochemistry | 37 |
| 5 | Cell Cycle, Cell Morphology, Cancer | 34 |

Table B is a summary of diseases and associated networks that are affected as a result in upregulation or downregulation of the summary from the RNA-Seq analysis. These top networks reveal that cancer cell metabolism (energy production) and proliferation are significantly affected by treatment with H.2. This effect could be amplified or inhibited based on the genes (molecules) involved. This output represents the top scoring diseases and networks as determined by the Ingenuity Pathway Analysis (Qiagen) software package.

Additionally, treatment of cancer cells with EPE001 resulted in over 2000 molecules that were upregulated or downregulated, many of which are involved in tumor suppression and inhibition of cell growth. Outside of cancer related networks, EPE001 also had an effect on genes associated with DNA replication, recombination and repair, embryonic development, nervous system development and function. These results would suggest an increase in stimulation of repair, stem cell activity, as well as stimulation of hair growth.

There was also an upregulation in genes associated with lipid metabolism which would suggest EPE001 would increase lipid metabolism. This has negative effects on cancer cells because they rely on carbohydrate metabolism for proliferation. This phenomenon also suggests that energy output would increase in healthy cells when using lipid substrates rather than carbohydrates because the process of β-oxidation yields ~4× as much energy as aerobic respiration (glucose-dependent).

VII. Preferred Embodiment-Emulsifier System

A preferred embodiment of the cream-based topical preparation of a cream consisting of an emulsifier system which may be alkanolamine soap, a borax-beeswax soap, nonionic constituents including polyol esters, esters, fatty acids, fatty alcohols, hexose derivative esters, alkyl phenols, lanolin alcohols and acids and cationics. The system contains emollients such as mineral oil, petrolatum, isopropyl esters, aliphatic alcohols, lanolin derivatives, long and branch chain alcohol and polyol esters, and triglycerides. The system also contains humectants such as glycerin, propylene glycol, sorbitol, polyethylene glycols, and methyl glucoside alkoxylates. The system contains skin healing agents such as Aloe Vera, allantoin, urea, silicone derivatives, and either natural product extracts or a protein or proteins from the tripartite motif family of proteins (TRIM). The system contains a preservative such as parabens, phenoxyethanol and selected inorganic salts may be present to act as an anti-microbial agent. Additional inorganic salts are included if required for the function of the active ingredient.

VIII. Alternative Preferred Embodiment-Hydrogel

In another preferred embodiment a hydrogel formulation is prepared by replacing the emulsifying agent with a gelling agent such as a carbomer, hydroxycellulose, guar derivatives, cross-linked acrylic acid polymers, or similar gelling agents. The hydrogel also contains emollients, humectants, preservatives, skin healing agents, and inorganic salts as described above.

In the preferred embodiments, the formulation can contain a variety of preservatives, solvents, binding agents, emulsion stabilizers, film formers, moisturizers, and other ingredients commonly used in cosmetic and healing creams.

An exemplary cream/lotion formulation may comprise about 40-70% deionized water, 5-20% emulsifying agents, 10-20% emollients, 10-20% humectants, 4-6% skin healing agents, 0.05-1.5% inorganic salts and 1-2% preservatives. The water, preservatives and water-soluble ingredients are heated to 65° C. In a separate tank the oil soluble ingredients are melted and then added to the water phase at 65° C. with vigorous mechanical stirring. Before the emulsion sets up as a cream, the skin conditioning agents are added with continued mixing until the cream comes to room temperature.

An exemplary hydrogel may be composed of 50-70 deionized water 2-5% gelling agent. 1-2.5% neutralizing agent, 10-20% emollients, 10-20% humectants, 4-6% skin healing agents, 0.05-1.5% inorganic salts, 1-2% preservatives. The gelling agent is slowly added over 60 minutes to the water/preservatives with vigorous mechanical stirring and then vigorously mixed for an additional 60 minutes. The humectants, emollients skin healing agents and inorganic salts are then added over 60 minutes. The solution is then neutralized, and the resulting gel is mixed and circulated for an additional 60 minutes.

The formulation and alternative embodiments presented have several attributes that are subject to claims. First, within the embodiment of the cream containing the emulsifier, the inclusion of the skin healing agents such as aloe vera, allantoin, urea, silicone derivatives, and an analgesic, such as lidocaine, natural product extracts or a protein or proteins from the tripartite motif family of proteins (TRIM) in different component percentages will increase the rate of wound repair by reducing inflammation, promoting epithelial cell migration, inhibiting fibrosis (formation of scar tissue via fibroblast secretion of collagen). Furthermore, the inclusion of a silver inorganic salt demonstrates well-established anti-microbial activity. The reduction of inflammation and inhibition of scar tissue formation further reduces the exudate generated at the site of the wound, promoting more rapid epithelialization across the wound.

Considering the aspect of penetrance, the emollients promote carriage of wound repair proteins through the upper layers of the epidermis (specifically the cornified layers) to the deeper layers (stratum germinativum) where cell replication and regeneration occurs. This is accomplished through the lipophilic nature of the emollients that act as carriers through the lipid bilayers of the cells as well as the basement membrane compartment formed by connective tissue associated proteins. This carrier trait is not only accomplished through lipophilicity, but also by charge. For instance, the isoelectric point of one TRIM family member, is 6.08. At physiological pH of blood (7.35) the net charge is negative. The cations contained within the formulation will help bind and carry these anionic molecules through the epidermal layer and into the dermal layer surrounding the wound.

Considering the aspects of the Hydrogel formulation, the replacement of the emulsifying agent with a gelling agent will promote matrix regeneration. The protein scaffold will be more rapidly secreted in the underlying connective tissue by the fibroblasts due to the presence of the gelling agent. This agent acts like a foundation upon which the secreted protein scaffold can anchor as the architecture of the wounded tissue is reconstructed.

The Hydrogel can also contain emollients, humectants, preservatives, skin repair agents, and inorganic salts as described in paragraph [[0060]] above, allowing for a multipronged approach to more rapid repair of the wound (e.g. promoting epithelialization, inhibiting fibrosis and laying down a basal layer for extracellular matrix protein scaffold formation.

In preferred embodiments, the inclusion of film formers, anti-caking agents, moisturizers, and other ingredients commonly used in cosmetic and repair creams will also increase the rate of wound repair in conjunction with the other ingredients. These components promote continued moisture, reducing/preventing wound desiccation which would inhibit repair because the cells would not be able to migrate across the wound area or lay down foundational proteins. Thus, the wound would be repaired more slowly from the deepest point of the wound instead of from the underlying layer and sides simultaneously.

Aspects discussed above involve external wounds only. This means wounds to the integument at the level of the epidermis, dermis and the hypodermis and does not include the underlying muscle layers.

IX. Examples and Results Utilizing the Emulsifier System

Figure 10:
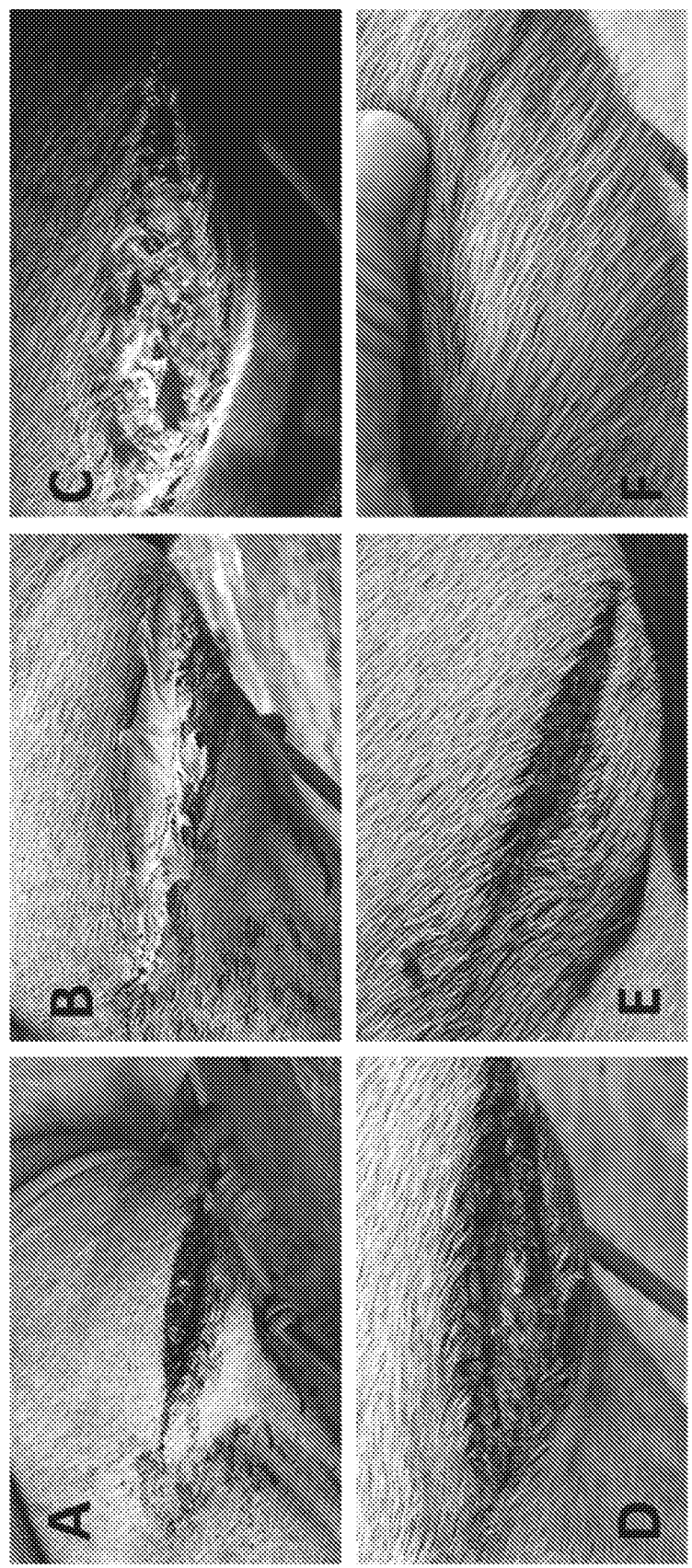
FIG. 10 is a series of images depicting the treatment of a wound on the cheek of a horse through the treatment course with the Emulsifier System containing a TRIM protein family member as the active ingredient.
Figure 11:
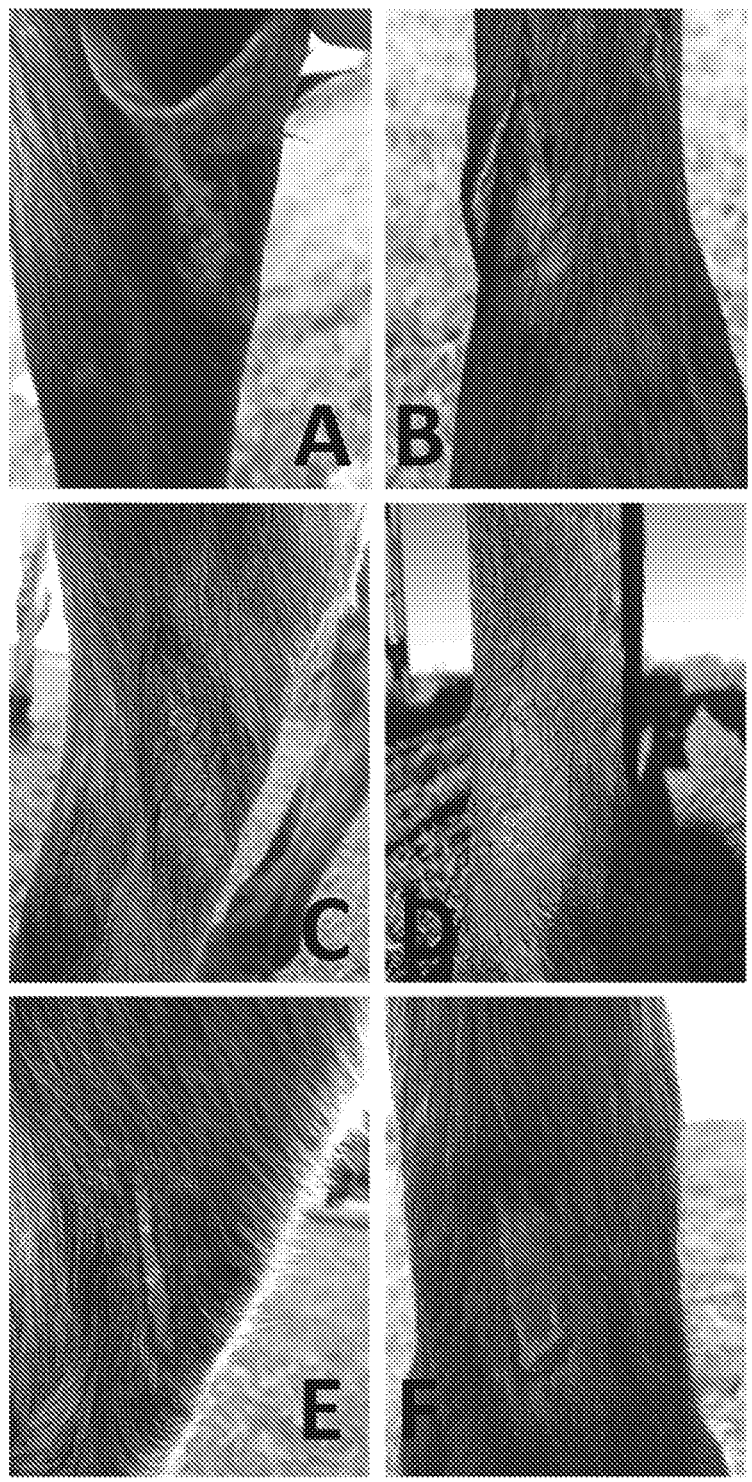
FIG. 11 is a series of images showing the treatment of a wound on the leg of a horse through the treatment course with the Emulsifier System containing a TRIM protein family member as the active ingredient.
Figure 12:
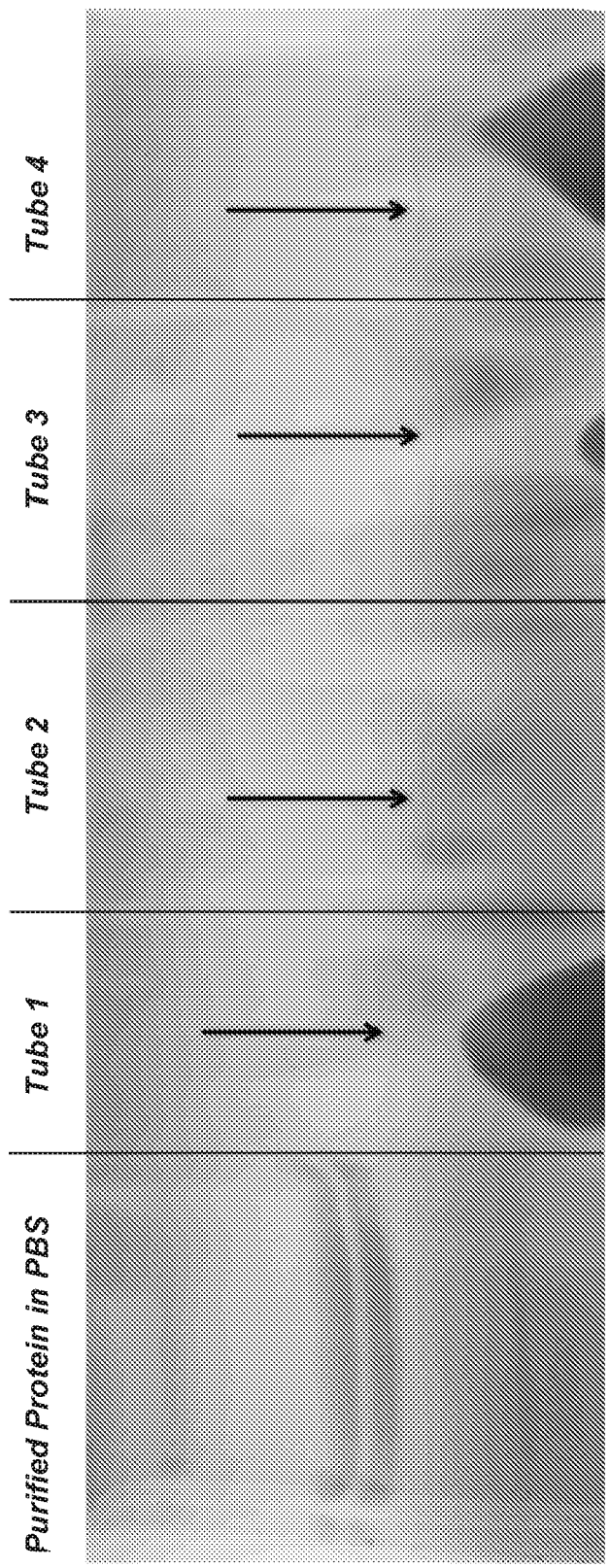
FIG. 12 is an SDS-PAGE gel showing the stability of the active ingredient after one year of being contained within the cream formulation.

FIGS. 10-12 show several examples and results thereof utilizing a product produced by the process described above. Other examples are not explicitly shown, but the results are described below. One particular preparation of the Emulsifier System contains the active ingredient TRIM-family member protein, MG53. Other ingredients: Deionized water, methyl paraben, phenoxyethanol, glycerine, urea, cetearyl alcohol/ceareth 20, mineral oil, lanolin oil, isopropyl myristate, propyl paraben, allantoin, dimethicone, silver nitrate and zinc chloride.

FIG. 10 is an example of wound treatment with the Emulsifier System containing a TRIM Family Member Protein as the active ingredient. Panel A shows a laceration on the cheek of an eleven-year-old quarter horse mare. Normally, a laceration of this magnitude would be sutured, instead the wound was left open to study the healing efficacy of the cream. The wound was not washed or disinfected prior to adding the cream. The wound was treated with the Emulsifier System containing TRIM Family Member Protein twice per day and was not washed or treated in any other way for the duration of healing. Panel B shows the application of the cream to the wound. The cream remained where it was applied and did not cause any irritation to the wound or surrounding areas. Panel C shows the wound at Day 4 where indications of the wound repair can be seen. Panel D shows the wound at Day 8. No serum drainage had been detected from the wound and appeared to undergo less debridement in the repair process than is typically seen. Panel E shows the wound on Day 15 where the wound has constricted considerably. Panel F shows the wound on Day 58 where the wound has been repaired and hair has regrown. The scar line is only barely visible. The main point is that the cream acted as a neutral carrier, did not cause inflammation, exudation or desiccation counterproductive to wound repair.

FIG. 11 is another example of wound treatment with the Emulsifier System containing a TRIM Family Member Protein as the active ingredient. Panels A and B show a wound on the leg of a horse that occurred when the horse kicked a fence. As in the previous example, the wound was not cleaned or disinfected (after initial washing) during the course of treatment with the Emulsifier System containing a TRIM Family Member Protein. The cream was applied to the wound twice per day and the wound was wrapped after application for the first week only. Panels C and D show the wound two weeks after the injury. Panels E and F show the wound one month after injury. The main point is that the cream acted as a neutral carrier, did not cause inflammation, exudation or desiccation counterproductive to wound repair.

X. Stability of Proteins Contained in the Cream-based Formulation

Stability is a major issue in incorporating recombinant proteins as active ingredients into a commercial product. Typically, purified proteins without any type of preservative will degrade within a few days and become inactive when left at room temperature. Using the formulations in the previous examples, the active ingredient, the TRIM Family Member protein, remains active for over one year when stored at room temperature. FIG. 12 shows the stability of the TRIM Family Member protein in the cream-based formulation. Samples were then prepared for analysis and loaded onto an SDS-PAGE gel.

The samples were: Lane 1 contains TRIM Family Member protein that was stored in Phosphate Buffered Saline (PBS) at 4° C. for 13 months. Lane 2-4 are samples of the cream-based formulation containing the TRIM Family Member protein. The arrows indicate the band corresponding to the molecular weight of TRIM Family Member protein in each of the samples in Lanes 2-4. In each of these samples, after more than one year, the active ingredient can still be detected by SDS-PAGE analysis, which means that the protein has not degraded during this timeframe. Furthermore, the protein remained more stable in the cream-based formulation at room temperature than the TRIM Family Member stored in PBS at 4° C. for the same timeframe. This is indicated by the lack of doublet bands in the cream samples. Thus, these formulations for the Emulsifier and Hydrogel are viable systems to maintain the activity of the active ingredient.

It is to be understood that while certain embodiments and/or aspects of the invention have been shown and described, the invention is not limited therein and encompasses various other embodiments and aspects.

Having thus described the invention, what is claimed as new and desired to be secured by Letters Patent is:

1. A topically-applied hydrogel for the treatment of inflammation, the topically-applied hydrogel comprising:
    a gelling agent;
    an emollient element;
    a humectant;
    a preservative; and
    an effective amount of an active ingredient mixture consisting of extracts of *Cinnamomum cassia, Arctium lappa, Vitex agnus castus, Lonicera japonica, Acanthopanax gracilistylis, Raphanus sativus, Astragalus membranaceus*, and *Hordeum vulgare*.

2. The topically-applied hydrogel of claim 1, further comprising an ingredient selected from the group consisting of: Aloe Vera, allantoin, urea, silicone derivatives, inorganic salts, natural product extracts and a protein or proteins from the tripartite motif family of proteins (TRIM).

3. The topically-applied hydrogel of claim 2, further comprising an anti-microbial element.

4. The topically-applied hydrogel of claim 2, wherein said preferred result comprises scarring-reducing properties.

5. The topically-applied hydrogel of claim 2, further comprising a topical analgesic.

6. The topically-applied hydrogel of claim 1, wherein:
    said active ingredient comprising an extraction mixture produced through an aqueous extraction process in an extraction vessel configured to store a fibrous container and a volume of water;
    a heating element configured to heat said volume of water within said extraction vessel, thereby creating water vapor and heated water;
    a dry mixture placed within said fibrous container, said dry mixture comprised of one or more elements selected from the group consisting of: *Cinnamomum cassia, Arctium lappa, Vitex agnus castus, Lonicera japonica, Acanthopanax gracilistylis, Raphanus sativus, Astragalus membranaceus* and *Hordeum vulgare;*
    said heated water configured to draw volatiles and said extraction mixture from said dry mixture;
    a condenser connected to said extraction vessel, said condenser configured to remove water vapor and volatiles; and
    said extraction mixture configured to be used as a treatment.

7. A method of treating a condition selected from a list consisting of: wounds, scarring, burns, itching, rashes or irritations, and cosmetic purposes, comprising administering an effective amount of the composition of claim 1.

* * * * *